US005590649A

United States Patent [19]
Caro et al.

[11] Patent Number: 5,590,649
[45] Date of Patent: Jan. 7, 1997

[54] APPARATUS AND METHOD FOR MEASURING AN INDUCED PERTURBATION TO DETERMINE BLOOD PRESSURE

[75] Inventors: Richard G. Caro; Mark H. Sher, both of San Francisco, Calif.

[73] Assignee: Vital Insite, Inc., So. San Francisco, Calif.

[21] Appl. No.: 228,213

[22] Filed: Apr. 15, 1994

[51] Int. Cl.⁶ ................................................. A61B 5/00
[52] U.S. Cl. ......................... 128/630; 128/633; 128/677; 128/680; 128/687; 128/716; 128/736; 128/748; 128/691; 128/672; 128/668
[58] Field of Search ................................. 128/632, 633, 128/630, 664–668, 672–694, 696, 713, 716, 719, 721, 722, 736, 748

[56] References Cited

U.S. PATENT DOCUMENTS

| | | |
|---|---|---|
| 3,090,377 | 5/1963 | Salisbury et al. |
| 3,095,872 | 7/1963 | Tolles. |
| 3,885,551 | 5/1975 | Massie. |
| 4,569,261 | 2/1986 | Penaz. |
| 4,646,754 | 3/1987 | Seale ........................................ 128/677 |
| 4,718,426 | 1/1988 | Russell ..................................... 128/681 |
| 5,241,963 | 9/1993 | Shankar .................................... 128/694 |
| 5,241,964 | 9/1993 | McQuilkin ............................... 128/672 |
| 5,267,565 | 12/1993 | Beard ....................................... 128/687 |

FOREIGN PATENT DOCUMENTS

0443267A1  8/1991  European Pat. Off. ...... A61B 5/0285

OTHER PUBLICATIONS

"Characteristics of Impact and Pulse Wave Propagation in Brachial and Radial Arteries;" M. Landowne; Journal of Applied Physiology, vol. 12, p. 91, 1958.

"Dispersion and Attenuation of Small Artificial Pressure Waves in the Canine Aorta;" M. Anliker, et al.; Circulation Research, Vo. XXIII, pp. 539–551, Oct. 1968.

"Measurement of Pulse–Wave Velocity Using a Beat–Sampling Technique;" J. D. Pruett, et al.; Annals of Biomedical Engineering, Vo. 16, pp. 341–347, 1988.

"Scientific and Engineering Instruments; Application Note #3 About Lock–In Amplifiers;" Stanford Research Systems, 1992 Catalog; pp. 129–139.

*Primary Examiner*—Angela D. Sykes
*Assistant Examiner*—Robert L. Nasser
*Attorney, Agent, or Firm*— Flehr, Hohbach, Test, Albritton & Herbert

[57] ABSTRACT

A monitor for continuously determining a patient's physiological parameter includes a means for obtaining a periodic calibration measurement of the patient's physiological parameter. An exciter, positioned over an artery of the patient induces an exciter waveform into the patient's arterial blood. A noninvasive sensor, positioned over the artery, senses a hemoparameter and provides a noninvasive sensor signal output representative of the hemoparameter. A processor receives the calibration measurement and noninvasive sensor signal output. The processor determines a DC offset based on the calibration measurement and processes the noninvasive sensor signal to continuously determine the patient's physiological parameter. A method includes steps for performing the present invention. In the preferred embodiment, the physiological parameter measured is blood pressure, however, the present invention can also be used to analyze and track other physiological parameters such as vascular wall compliance, strength of ventricular contractions, vascular resistance, fluid volume, cardiac output, myocardial contractility and other related parameters.

26 Claims, 9 Drawing Sheets

APPARATUS AND METHOD FOR MEASURING AN INDUCED PERTURBATION TO DETERMINE BLOOD PRESSURE

FIELD OF THE INVENTION

The present invention relates to an apparatus and method for noninvasively providing a continuous measure of a patient's blood pressure and other clinically important parameters.

BACKGROUND OF THE INVENTION

Blood pressure is the force within the arterial system of an individual that ensures the flow of blood and delivery of oxygen and nutrients to the tissue. Prolonged reduction or loss of pressure severely limits the amount of tissue perfusion and could therefore result in damage to or even death of the tissue. Although some tissues can tolerate hypoperfusion for long periods of time, the brain, heart and kidneys are very sensitive to a reduction in blood flow. Thus, during and after surgery, blood pressure is a frequently monitored vital sign. Blood pressure is affected, during and after surgery, by the type of surgery and physiological factors such as the body's reaction to the surgery. Moreover, blood pressure is manipulated and controlled, during and after surgery, using various medications. Often, these physiological factors and the given medications can result in a situation of rapidly changing blood pressure requiring immediate blood pressure measurement, and corrective action.

Because of changes in the patient's blood pressure, constant monitoring is important. The traditional method of measuring blood pressure is with a stethoscope, occlusive cuff and pressure manometer. However, this technique is slow, subjective in nature, requires the intervention of a skilled clinician and does not provide timely readings frequently required in critical situations.

For these reasons, two methods of measuring blood pressure have been developed: noninvasive, intermittent methods that use an automated cuff device such as an oscillometric cuff; and invasive, continuous (beat-to-beat) measurements that use a catheter.

The oscillometric cuff method typically requires 15 to 45 seconds to obtain a measurement, and should allow sufficient time for venous recovery. Thus, at best there is typically ½ to 1 minute between updated pressure measurements. This is an inordinately long amount of time to wait for an updated pressure reading when fast acting medications are administered. Also, too frequent cuff inflations over extended periods may result in ecchymosis and/or nerve damage in the area underlying the cuff. The invasive method has inherent disadvantages including risk of embolization, infection, bleeding and vessel wall damage.

To address the need for continuous, noninvasive blood pressure measurement, several systems were developed. One system relies on blood pressure values in a patient's finger as indicative of the patient's central blood pressure. Another system uses two cuffs, one on each arm, to determine calibration readings and continuous readings respectively. Another system transforms a time sampled blood pressure waveform into the frequency domain and determines blood pressure based on deviations of the fundamental frequency. Kaspari, et al. U.S. Pat. application Ser. No. 08/177,448, filed Jan. 5, 1994 provides examples of these systems.

A related area of interest was explored by perturbing the body tissue of patients. One class of experiments causes perturbations by inducing kinetic energy into the patient, specifically, by oscillating a blood vessel. Several experiments measured the velocity of excited perturbations in the blood and demonstrated a correlation between perturbation velocity and blood pressure. Such a correlation has also been demonstrated between pressure and the velocity of the natural pulse wave. However, while these studies discuss the relationship between velocity and pressure they do not propose a practical method of measuring induced perturbations to determine blood pressure. Examples of such studies are M. Landowne, *Characteristics of Impact and Pulse Wave Propagation in Brachial and Radial Arteries*, J. Appl. Physiol., vol. 12, p. 91 (1958); J. Pruett, *Measurement of Pulse-Wave Velocity Using a Beat-Sampling Technique*, Annals of Biomedical Engineering, vol. 16, p. 341 (1988); and M. Anliker, *Dispersion and Attenuation of Small Artificial Pressure Waves in the Canine Aorta*, Circulation Research, vol. 23, p. 539 (October 1968).

OBJECTS AND SUMMARY OF THE INVENTION

The present invention describes an apparatus and method for measuring the induced perturbation of a patient's body tissue to determine the patient's blood pressure and other clinically important parameters.

An object of the present invention is to continuously determine a patient's blood pressure via a noninvasive sensor attached to the patient.

A related object is to induce a perturbation into a patient's blood or blood vessel and to noninvasively measure the perturbation to determine the patient's blood pressure.

A related object is to filter the noninvasive sensor signal into constituent components including a natural component, an induced component and a noise component, and to determine the patient's blood pressure from the natural component and the induced component.

A monitor for continuously determining a patient's blood pressure includes calibration means for obtaining a periodic calibration signal representing the patient's blood pressure. An exciter, positioned over a blood vessel of the patient induces an exciter perturbation into the patient. A noninvasive sensor positioned over the blood vessel senses a hemoparameter and generates a noninvasive sensor signal output representative of the hemoparameter. In this context, a hemoparameter is any physiological parameter related to blood such as pressure, flow, volume, velocity, blood vessel wall motion, blood vessel wall position and other related parameters. A processor, connected to the calibration means and the noninvasive sensor signal output, receives the calibration measurement and processes the noninvasive sensor signal to continuously determine the patient's blood pressure. A method includes steps for performing the present invention.

DETAILED DESCRIPTION OF THE PREFERRED EMBODIMENTS

A preferred embodiment concentrates on the physiological parameter of blood pressure, however, many additional physiological parameters can be measured with the present invention including vascular wall compliance, ventricular contractions, vascular resistance, fluid volume, cardiac output, myocardial contractility and other related parameters. Those skilled in the art will appreciate that various changes and modifications can be made to the preferred embodiment while remaining within the scope of the present invention. As used herein, the term continuous means that the physiological parameter of interest is determined over a period of time, such as during the course of surgery. The implementation of portions of the invention in a digital computer is performed by sampling various input signals and performing the described procedures on a set of samples. Hence, a periodic determination of the physiological parameter of interest is within the definition of the term continuous.

Figure 1:
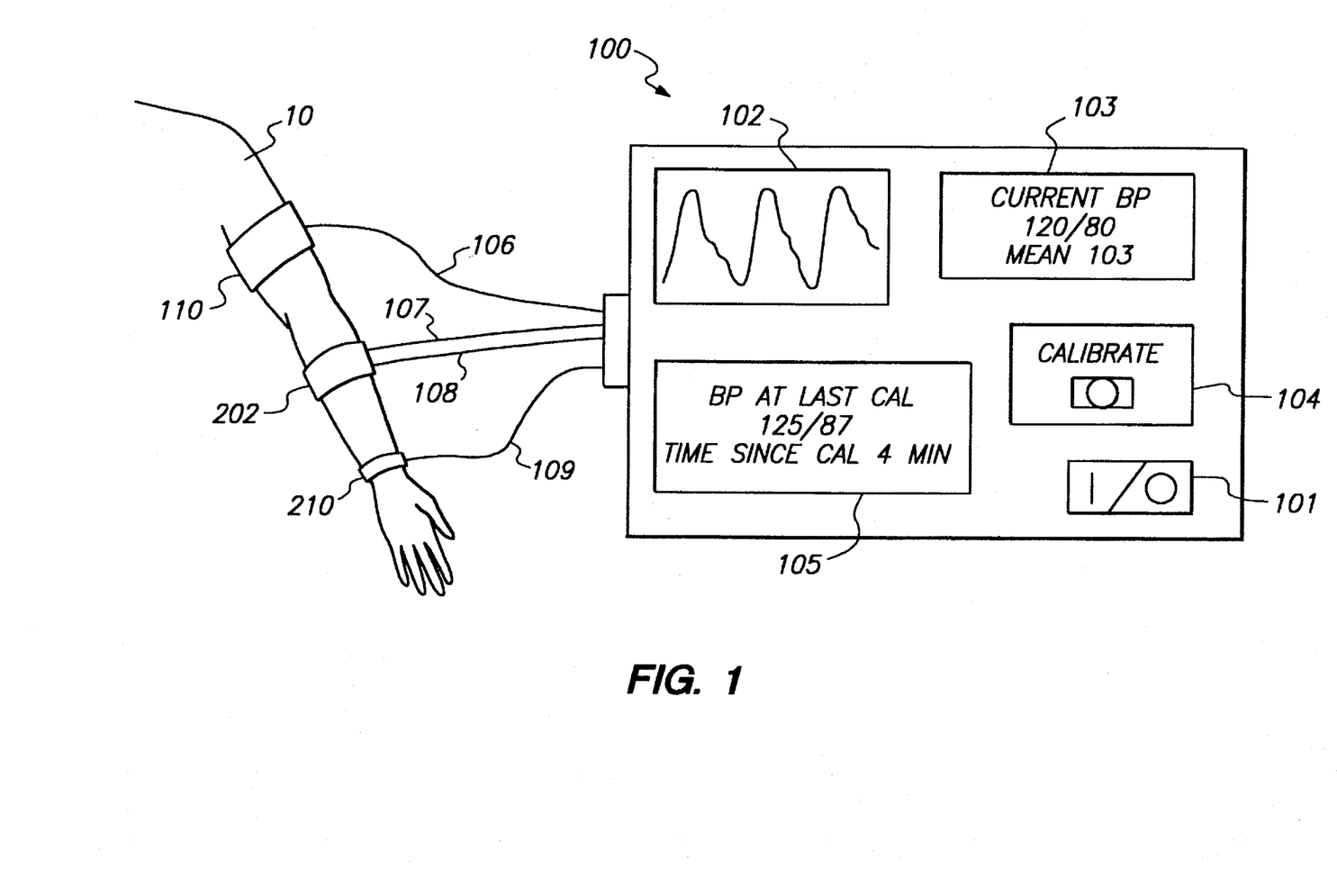
FIG. 1 depicts the present invention attached to a patient.

FIG. 1 illustrates the components and configuration of the preferred embodiment. Oscillometric cuff 110 is connected to processor 100 via wire 106, and cuff 110 is responsive to processor 100 during an initial calibration step. Oscillometric cuff operation, which is known in the art, involves an automated procedure for obtaining a blood pressure signal. The general procedure is given for clarity but is not crucial to the invention.

First, an occlusive cuff is pressurized around the patient's upper arm to abate the blood flow. Then, as the pressure is slowly reduced, a transducer senses when the blood flow begins and this pressure is recorded as the systolic pressure. As the pressure is further reduced, the transducer similarly detects the pressure when full blood flow is restored and this pressure is recorded as the diastolic pressure. The signals representing pressure are delivered, via wire 106, to processor 100 for storage.

FIG. 1 shows an exciter 202 attached to the patient's forearm above the radial artery. The exciter 202 is a device for inducing a perturbation of the patient's body tissue, and is controlled by the processor 100 via tube 107.

Figure 2:
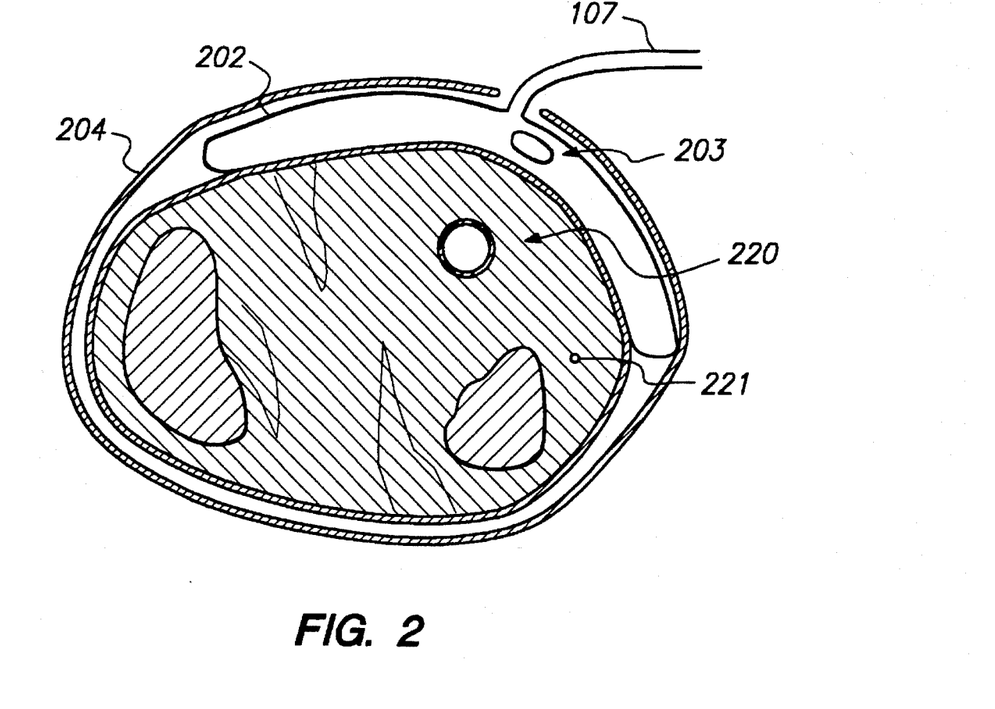
FIG. 2 depicts an exciter attached to a patient.

FIG. 2 shows a cross section of the exciter and its components. The exciter 202 is an inflatable bag attached to the processor via air tube 107. It is fixed in place near an accessible artery 220 by holddown device 204 which can be a buckle, adhesive strap or other device. There is also an exciter sensor 203 disposed within the exciter to generate a reference signal indicative of the perturbation source waveform, and to deliver the signal to the processor via wire 108. This signal is used as a reference signal by the processor (explained below).

As mentioned above, processor 100 is attached to the exciter via tube 107. The processor 100 controls the pressure in exciter 202 with a transducer and diaphragm. A transducer is a device that transforms an electrical signal to physical movement, and a diaphragm is a flexible material attached to the transducer for amplifying the movement. An example of this combination is a loudspeaker. The diaphragm forms part of an airtight enclosure connected to air tube 107 and an input to initialize the pressure.

In operation, the pressure is initially established via the initialization input and then the pressure is varied by an electrical signal delivered to the transducer; the diaphragm produces pressure variations in the tube in response to the transducer movement. The result is that the processor, by delivering an oscillating electrical signal to the transducer, causes oscillating exciter pressure. The exciter responds by perturbing the patient's tissue and inducing a transmitted exciter waveform into the patient.

The perturbation excites the tissue 221 and blood vessel 220 below the exciter and causes a the transmitted exciter waveform to radiate within the patient's body, at least a portion of which travels in the arterial blood. The excitation waveform can be sinusoidal, square, triangular, or of any suitable shape. Experiments conducted to determine a range of satisfactory perturbation frequencies found that the range of 20–600 Hz works well. It is anticipated that frequencies of lesser than 20 Hz and greater than 600 Hz will also work well, and it is intended that this specification cover all frequencies insofar as the present invention is novel.

FIG. 1 further shows a noninvasive sensor 210 placed at a distance from the exciter on the patient's wrist. The noninvasive sensor is connected to the processor 100 via wire 109.

Figure 3:
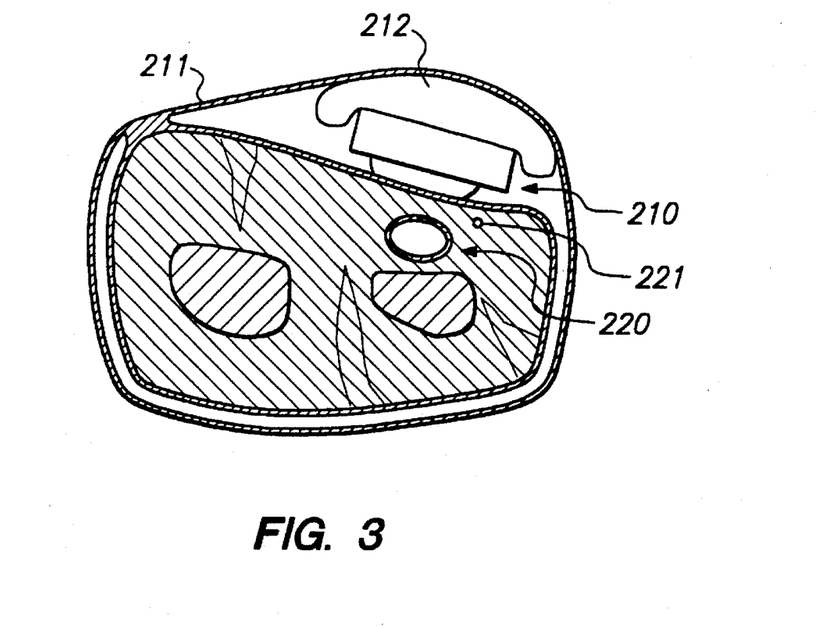
FIG. 3 depicts a noninvasive sensor attached to a patient.

FIG. 3 shows a cut-away view of the noninvasive sensor 210 placed over the same radial artery 220 as the exciter. The sensor 210 is fixed in place near the artery 220 by holddown device 211 which can be a buckle, adhesive strap or other device. The holddown device 211 also includes a baffle 212 to reduce noise, where the baffle is a pneumatic bag pressurized to hold the sensor 210 at a constant pressure against the patient, for example at a pressure of 10 mm Hg. Alternately, baffle 212 can be any suitable device such as a spring or foam pad.

The noninvasive sensor 210 is responsive to at least one hemoparameter of the patient and generates a signal in response thereto. In this context, a hemoparameter is defined as any physiological parameter related to vessel blood such as pressure, flow, volume, velocity, blood vessel wall motion, blood vessel wall position and other related parameters. In the preferred embodiment a piezoelectric sensor is used to sense arterial wall displacement, which is directly influenced by blood pressure.

As is shown, the sensor is positioned over the radial artery 220 and it is responsive to pressure variations therein; as the pressure increases, the piezoelectric material deforms and generates a signal corresponding to the deformation. The signal is delivered to the processor 100 via wire 109.

FIG. 1 also shows the processor 100 that has a control panel for communicating information with the user. A power switch 101 is for turning the unit on. A waveform output monitor 102 displays the continuous blood pressure waveform for medical personnel to see. A digital display 103 informs the user of the current blood pressure; there is a systolic over diastolic and mean pressure shown. A calibrate button 104 permits the user to calibrate the processor at any time, by pressing the button. The calibration display 105 shows the user the blood pressure at the most recent calibration, and also the elapsed time since calibration. The processor maintains a record of all transactions that occur during patient monitoring including calibration blood pressure, calibration times, continuous blood pressure and other parameters, and it is anticipated that additional information can be stored by the processor and displayed on the control panel.

Turning to the noninvasive sensor signal, in addition to a natural hemoparameter, the noninvasive sensor signal contains a component indicative of the exciter waveform travelling through the patient. Although the exciter component is designed to be small in comparison to the natural hemoparameter, it contains valuable information. Therefore, the processor is used to separate the exciter waveform from the natural hemoparameter, and to quantify the respective components to determine the patient's blood pressure.

Figure 4A:
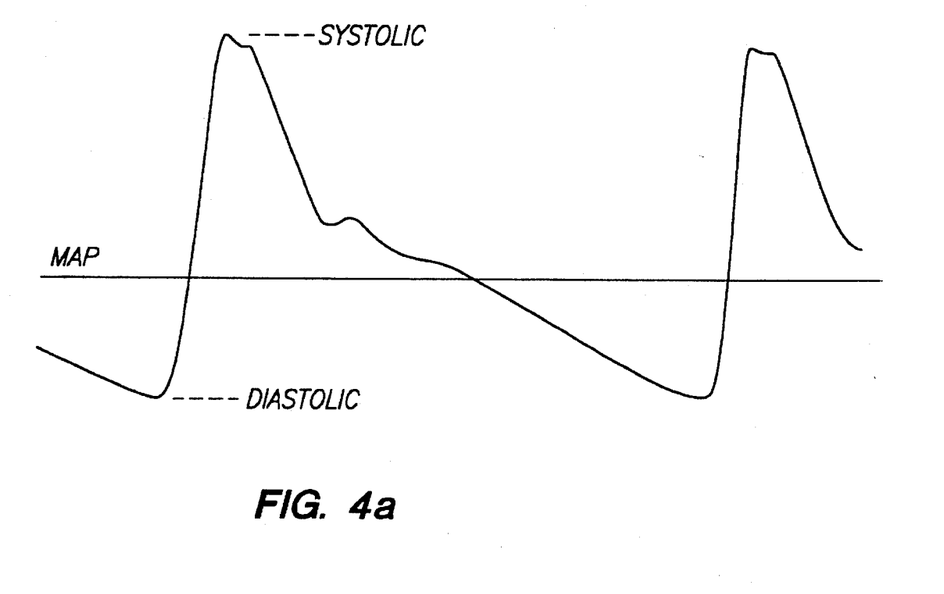
FIG. 4a depicts a blood pressure waveform.

FIG. 4a shows a natural blood pressure waveform where the minimum represents the diastolic pressure and the maximum represents the systolic pressure. This waveform has a mean arterial pressure (MAP) that is a convenient reference for purposes of determining the DC offset of the waveform. Example pressure values are 80 mm Hg diastolic and 120 mm Hg systolic respectively with a MAP DC offset of 90 mm Hg.

Figure 4B:
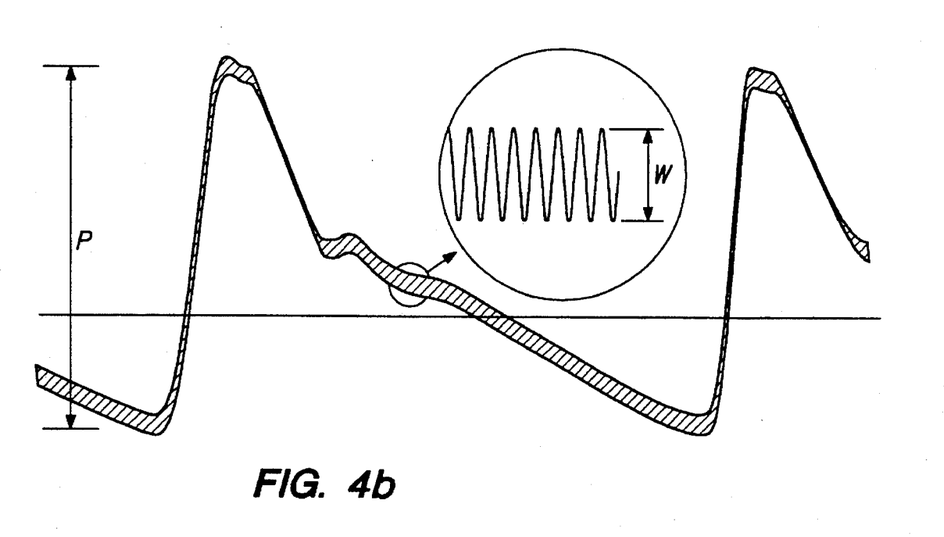
FIG. 4b depicts a blood pressure waveform with an exciter waveform superimposed thereon.

FIG. 4b shows an operational illustration of the arterial waveform; an exciter waveform superimposed on a natural blood pressure waveform. The exciter induces the exciter waveform into the arterial blood at a first location and the exciter waveform becomes superimposed on the natural waveform. Since the exciter waveform is small compared to the patient's natural waveform, the natural waveform dominates as shown in FIG. 4b. As mentioned above, the noninvasive sensor signal contains information regarding both the natural waveform and the exciter waveform. The processor 100 is designed to separate the constituent components of the noninvasive sensor signal to continuously determine the patient's blood pressure, as is discussed below.

Figure 5:
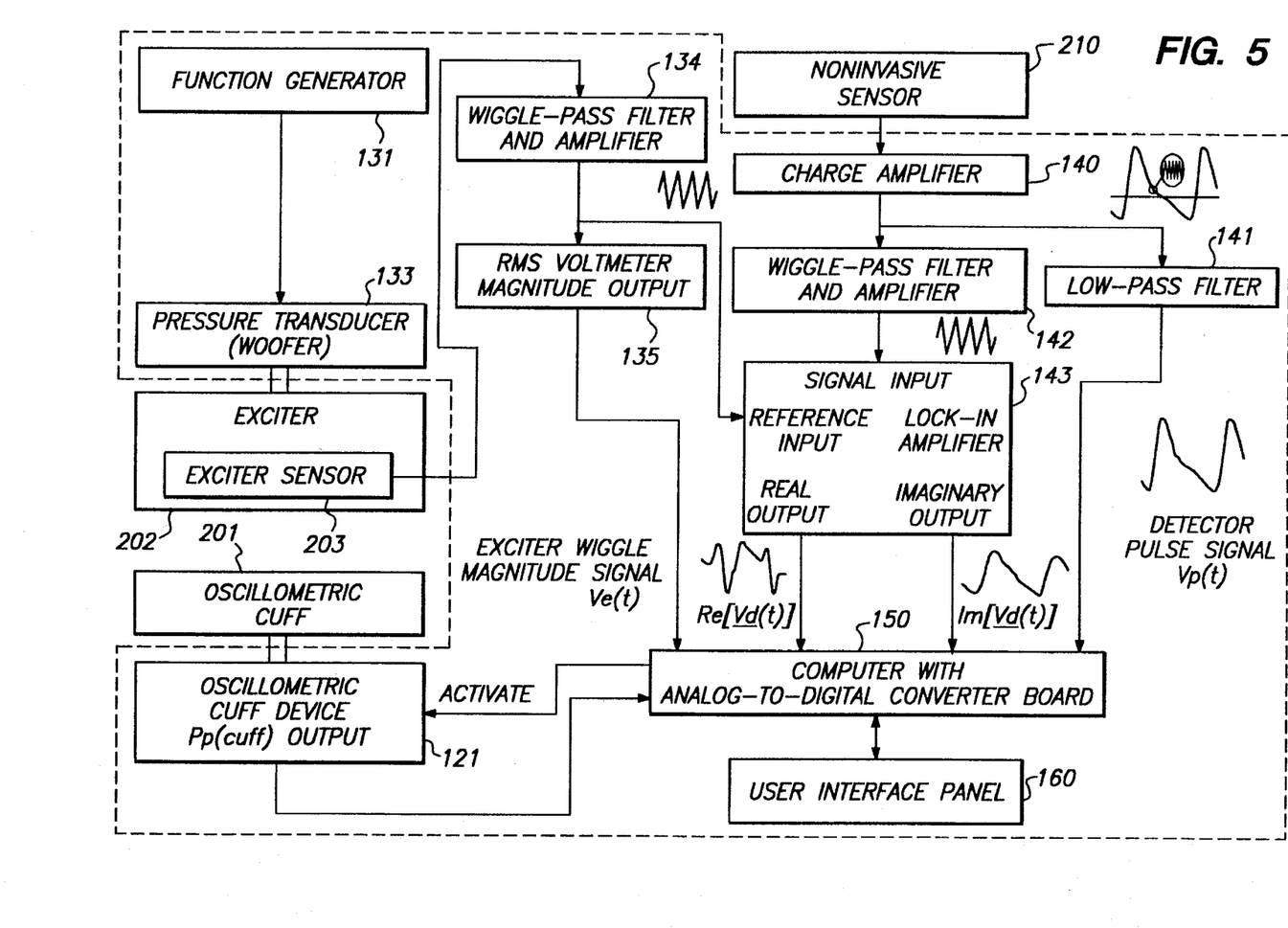
FIG. 5 depicts a schematic diagram of the present invention.

FIG. 5 depicts a schematic diagram of the preferred embodiment. There is an oscillometric cuff controller 121 for controlling the oscillometric cuff and determining the readings therefrom to generate a signal representing the patient's blood pressure. There is an induced wave frequency generator 131 coupled to a pressure transducer 133 that transforms an electrical input to a pressure output. The transducer output is connected to the exciter 202 and controls the exciter's oscillations for inducing the exciter waveform into the patient's arterial blood.

The output of the exciter sensor 203 is fed to a band pass filter 134. This filter 134 separates the high frequency signal responsive to the transducer pressure and delivers the resulting signal to RMS meter 135 and to lock-in amplifier 143 reference input. In the preferred embodiment, the RMS meter output is sampled at a rate of 200 samples per second with a 14 bit resolution and delivered to computer 150. It is anticipated that the sampling rate and resolution can be varied with good results.

The output of the noninvasive sensor is fed to a charge amplifier 140 that delivers a resulting signal to a low pass filter 141 and a band pass filter 142. These filters separate the noninvasive sensor signal into two constituent components representing an uncalibrated natural blood pressure wave and a received exciter waveform respectively. The low pass filter output is sampled at a rate of 200 samples per second with 14 bit resolution and delivered to computer 150, and the band pass filter output is delivered to the lock-in amplifier 143 signal input.

The lock-in amplifier 143 receives inputs from band pass filter 134 as reference and band pass filter 142 as signal, which are the exciter sensor signal and noninvasive sensor exciter signal respectively. The lock-in amplifier uses a technique known as phase sensitive detection to single out the component of the noninvasive sensor exciter signal at a specific reference frequency and phase, which is that of the exciter sensor signal. The amplifier 143 produces an internal, constant-amplitude sine wave that is the same frequency as the reference input and locked in phase with the reference input. This sine wave is then multiplied by the noninvasive sensor exciter signal and low-pass filtered to yield a signal proportional to the amplitude of the noninvasive sensor signal multiplied by the cosine of the phase difference between the noninvasive exciter signal and the reference. This is known as the in-phase or real output.

The amplifier 143 also produces an internal reference sine wave that is 90 degrees out-of-phase with the reference input. This sine wave is multiplied by the noninvasive sensor exciter signal and low-pass filtered to yield a signal proportional to the amplitude of the noninvasive sensor signal multiplied by the sine of the phase difference between the noninvasive sensor exciter signal and the reference. This is known as quadrature or imaginary output. The amplifier 143 then provides the computer 150 with information regarding the real and imaginary components of the noninvasive sensor exciter signal as reference to the phase of the exciter sensor signal. Alternately, the amplifier can provide components representing the magnitude and phase of the noninvasive sensor exciter signal. In the preferred embodiment, the amplifier output is sampled at a rate of 200 samples per second with a 14 bit resolution. It is anticipated that the sampling rate and resolution can be varied with good results.

The computer 150 receives input from the oscillometric cuff controller 121, RMS meter 135, low pass filter 141 and lock-in amplifier 150. The computer 150 also receives input from the user interface panel 160 and is responsible for updating control panel display information. The computer 150 executes procedures for further separating constituent components from the noninvasive sensor signal and attenuating the noninvasive sensor noise component as shown in FIG. 6.

Figures 6, 6A:
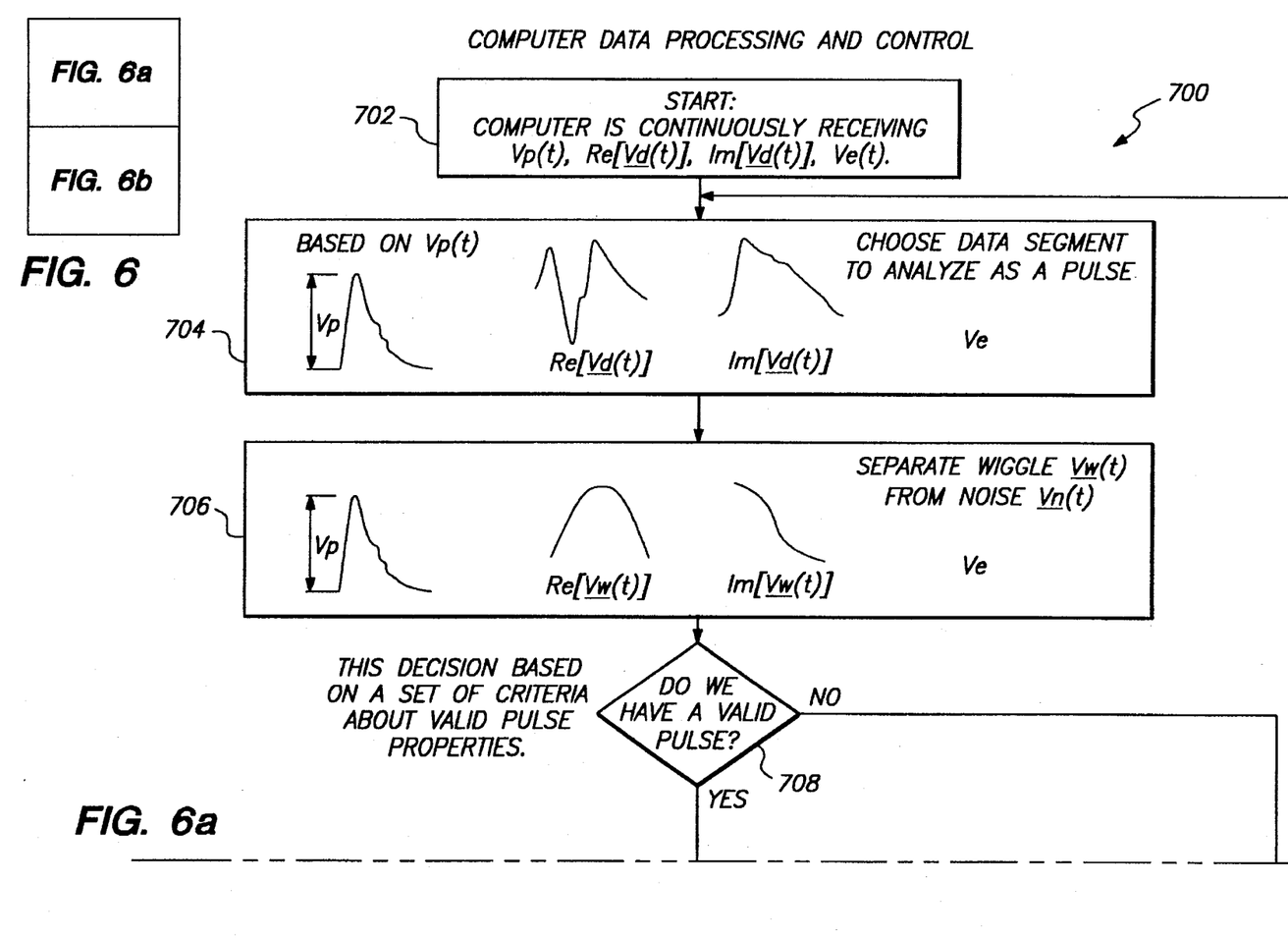
FIG. 6 depicts a processing flow chart of the present invention.
Figure 6B:
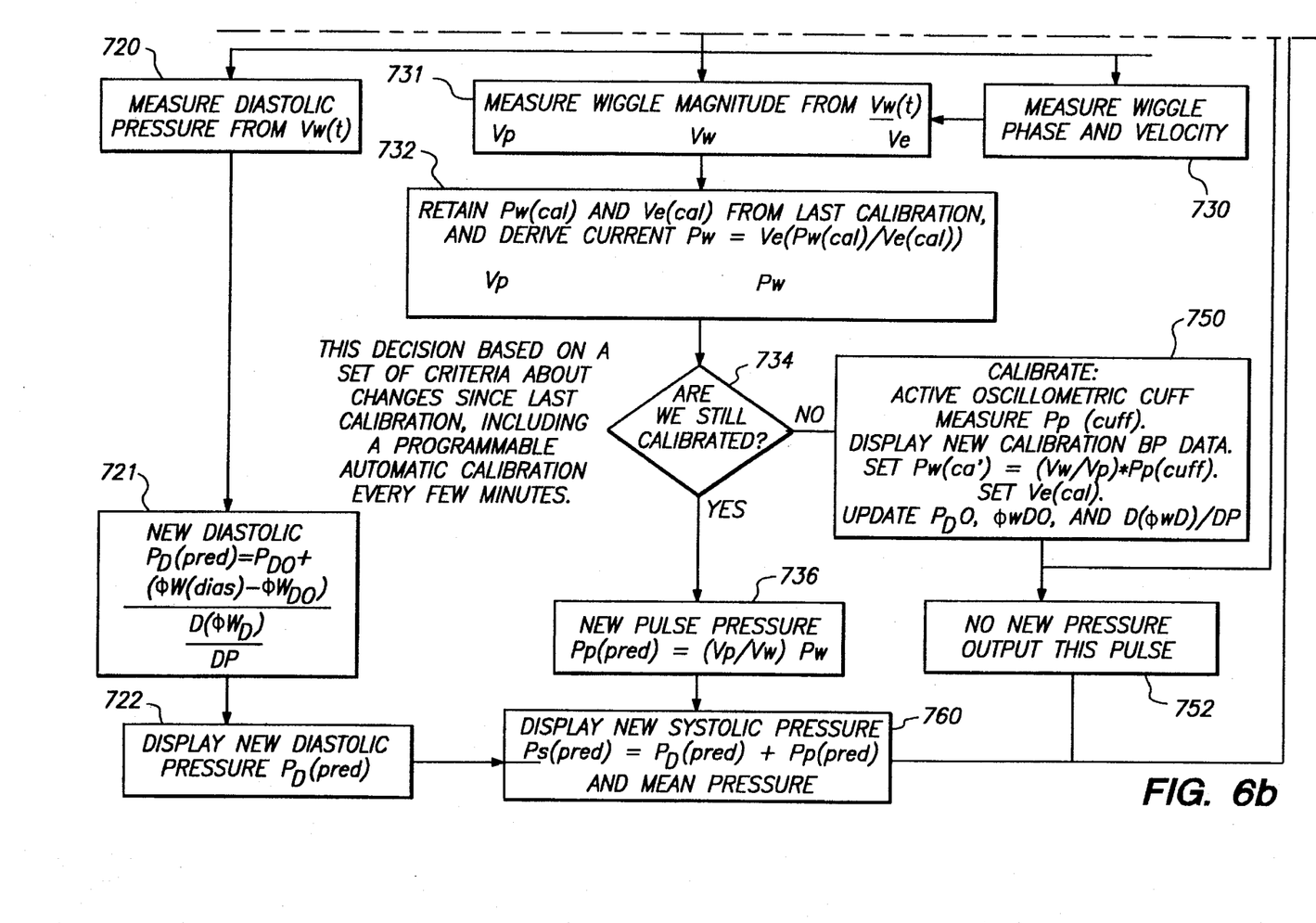

FIG. 6 is a processing flowchart that represents the operation of the FIG. 5 computer 150. The operation begins at step 702 with the receipt of an initial calibration measurement; noninvasive sensor signal and exciter sensor signal. Step 704 chooses the blood pressure waveform segment for pulse reference, which is important for continuity of measurement from pulse to pulse and for consistency over periods of time between calibration measurements. In the preferred embodiment, the diastolic pressure (low-point) is chosen for purposes of simplicity, but any point of the waveform can be chosen such as the systolic pressure or mean arterial pressure (MAP). The choice of the segment will relate to the DC offset discussed below.

Figure 7A:
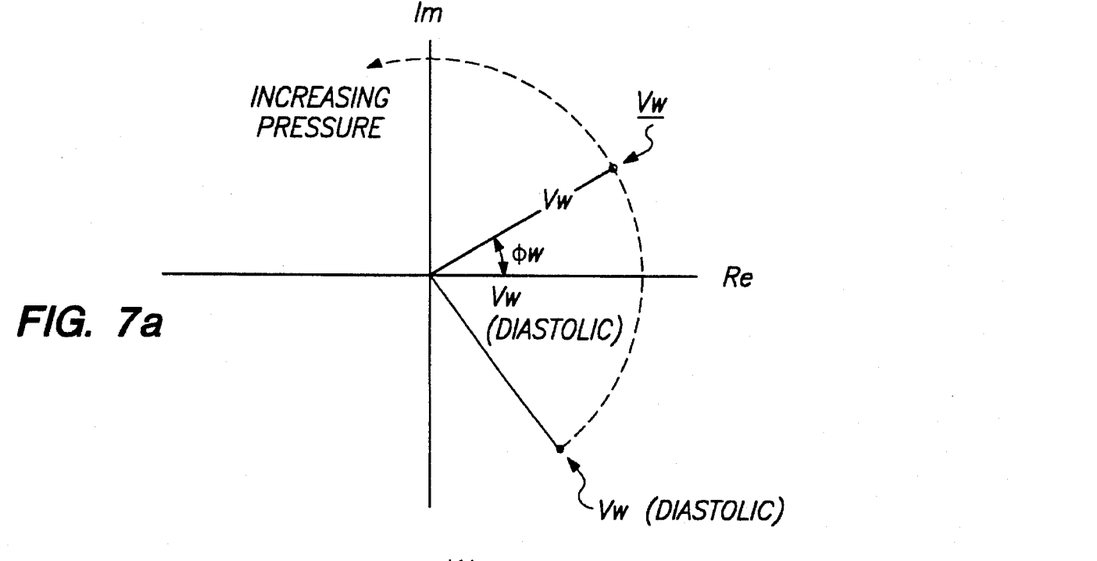
FIGS. 7a–c are graphical illustrations of the filter procedures of the present invention.
Figure 7B:
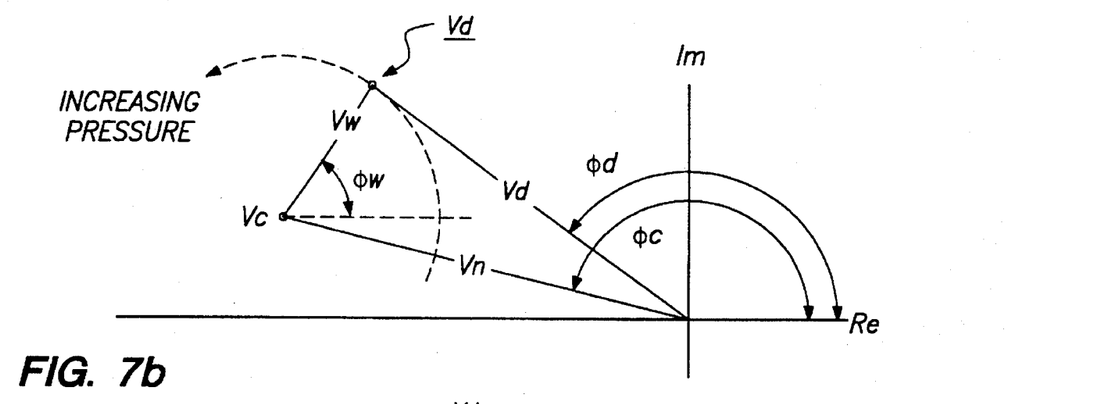
Figure 7C:
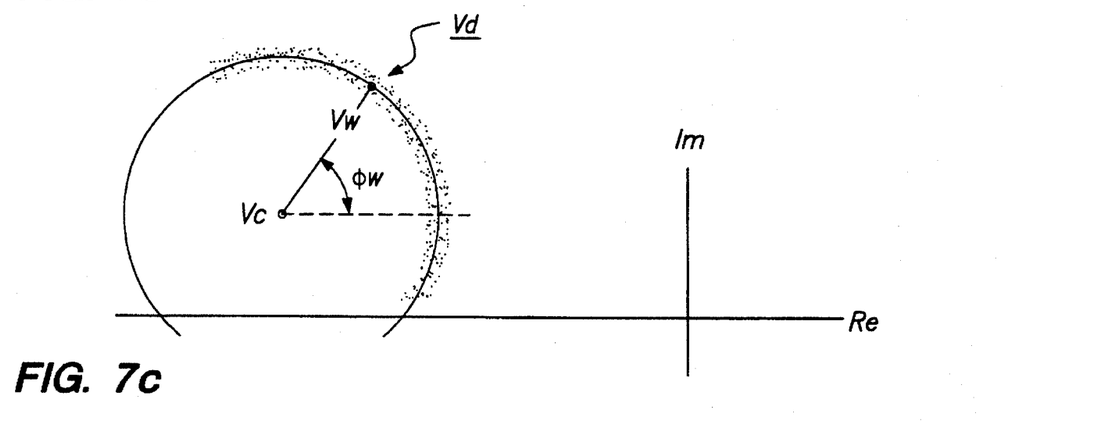

Step 706 is a filter step where the noninvasive sensor received exciter waveform is separated into a signal exciter waveform and noise components. The noise components may have many sources, one of which is a signal derived from the exciter that travels to the noninvasive sensor by an alternate path, other than that along the artery taken by the signal of interest. Examples include bones conducting the exciter waveform and the surface tissue such as the skin conducting the exciter waveform. FIGS. 7a–c illustrate the principles of the noninvasive sensor exciter signal filtering. During a natural pulse, a collection of points are generated in the complex plane by the real and imaginary outputs of the lock-in amplifier 143 which is monitoring the noninvasive sensor signal. FIG. 7a represents the noninvasive sensor exciter waveform in the absence of noise. A vector $V_w(t)$ has a magnitude and phase corresponding to the noninvasive sensor exciter signal. During a pulse, the magnitude of $V_w(t)$ remains constant, but the angle periodically oscillates from a first angle representing a lesser pressure to a second angle representing a greater pressure. Note that in the absence of noise, the arc has a center at the origin.

FIG. 7b represents the noninvasive sensor exciter waveform in the presence of noise, which is indicated by vector Vn. A vector $V_d$ has a magnitude and phase according to the noninvasive sensor exciter waveform plus noise. As can be seen in FIGS. 7b–c, vector $V_d(t)$ defines a collection of points forming an arc having a common point $V_c$ equidistant from each of the collection of points. The vector $V_w(t)$ from $V_c$ to the arc corresponds to the true magnitude and phase of the noninvasive sensor signal exciter waveform. While in many cases the arc will be a circle segment curve, in other cases the arc will deviate from a circle segment. The vector $V_n$ represents noise and, once identified, can be removed from the noninvasive sensor waveform. The filter step removes the $V_n$ component and passes the $V_w(t)$ component on to step 708.

Step 708 determines if the pulse is valid. To do this, the processor checks the constituent components of the noninvasive sensor signal to insure that the components are within acceptable clinical norms of the patient. For example, the processor can determine whether the new pulse is similar to the prior pulse, and if so, the new pulse is valid.

Figure 8A:
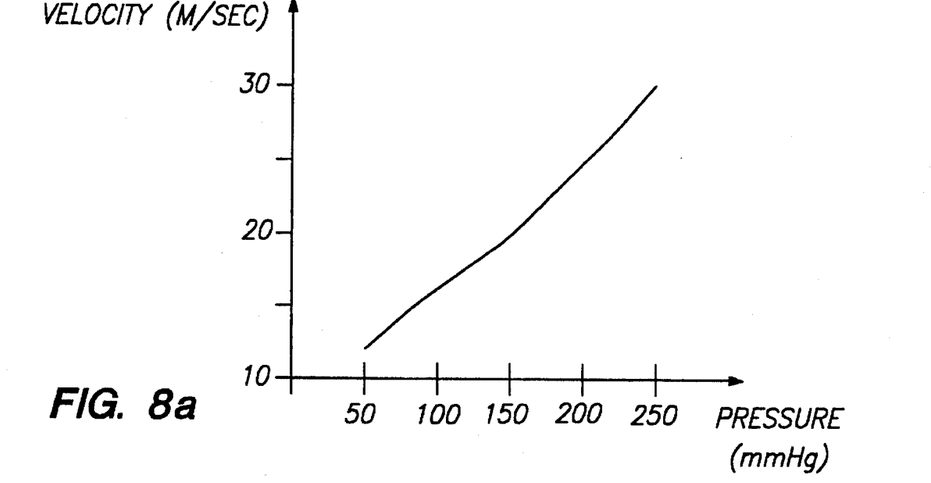
FIGS. 8a–c are graphical illustrations showing the relationships between the exciter waveform and blood pressure.
Figure 8B:
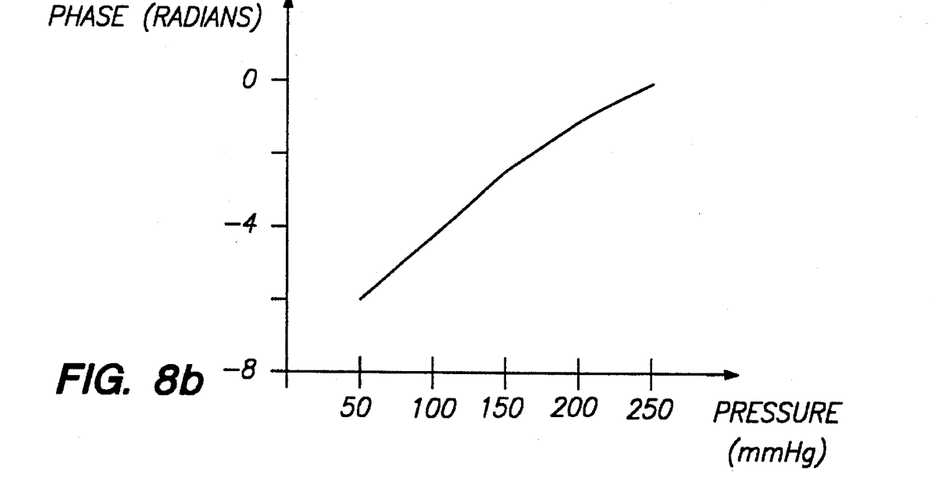
Figure 8C:
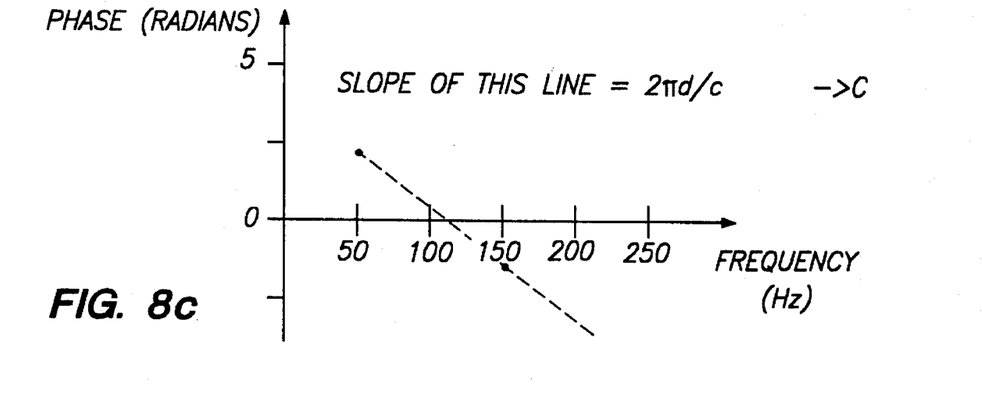

Step 720 processes the noninvasive sensor signal exciter waveform $V_w(t)$ to determine the DC offset. For convenience the diastole is used as the offset value, but any part of the waveform can be used. The processor determines the offset when the vector $V_w(t)$ reaches its lowest phase angle (i.e. the maximum clockwise angle of FIG. 7a); this is the diastole phase angle $\Phi w(dias)$. A calibration diastolic measurement is stored by the processor at calibration as $P_{D0}$. Also stored by the processor is a table denoting the relationship between the velocity of an exciter wave and blood pressure. This table is determined by reference to a sample of patients and is continuously updated by reference to the particular patient after each calibration measurement. FIG. 8a–c are graphical illustrations showing clinically determined relationships between the exciter waveform and blood pressure. FIG. 8b represents the relationship between phase and pressure at a frequency of 150 Hz; other frequencies have relationships that are vertically offset from the line shown. The velocity/pressure table represents the storage of this graphical information.

Step 721 determines the predicted diastolic pressure from the information in Step 720. The processor continuously determines the change in diastole from one pulse to the next by referencing the position of the noninvasive sensor exciter vector $V_w(t)$, at $\Phi w(dias)$, with respect to the stored velocity/pressure table. Moreover, the velocity/pressure table is continuously updated based on calibration measurement information gained from past calibrations of the patient.

A set of established relationships is used to develop and interpret information in the table and to relate the information to the sensor signal components. First, a known relationship exists between blood pressure and exciter waveform velocity. Also, at a given frequency many other relationships are known: a relationship exists between velocity and wavelength, the greater the velocity the longer the wavelength; and a relationship exists between wavelength and phase, a change in wavelength will result in a proportional change in phase. Hence, a relationship exists between blood pressure and phase, and a change in blood pressure will result in a proportional change in phase. This is the basis for the offset prediction.

With the stored calibration measurement plus the change in diastole, the new DC offset diastolic pressure is predicted $P_D(pred)$. This prediction is made based on the diastolic pressure at calibration $P_{D0}$ plus the quotient of the phase difference between calibration $\Phi w_{D0}$ and the present time $\Phi w(dias)$ and the velocity/pressure relationship table stored in processor memory as rate of change of exciter waveform phase to pressure $D(\Phi w_D)/DP$.

$$P_D(pred) = P_{D0} + \frac{(\Phi w(dias) - \Phi w_{D0})}{D(\Phi w_D)/DP}$$

Step 722 displays the predicted diastolic pressure.

Step 730 determines the noninvasive sensor exciter waveform phase and velocity. This determination is made based on the comparison of the noninvasive sensor exciter waveform with the exciter sensor waveform.

Step 731 determines the noninvasive sensor exciter waveform amplitude from the noninvasive sensor signal.

Step 732 determines the exciter waveform pressure $P_w$ by multiplying the exciter sensor waveform magnitude $V_e$ by the ratio of the calibrated exciter waveform pressure $P_w(cal)$ to the calibrated exciter sensor waveform magnitude $V_e(cal)$.

$$P_w = V_e * \frac{P_w(cal)}{V_e(cal)}$$

Step 734 determines if the calibration values are still valid. This determination can be based on many factors including the time since the last calibration, that the linearity of the velocity/pressure table is outside of a reliable range, determination by medical personnel that a new calibration is desired or other factors. As an example of these factors, the preferred embodiment provides user settable calibration times of 2, 5, 15, 30, 60 and 120 minutes, and could easily provide more. Moreover, the curve upon which the pressure is determined is piecewise linear with some degree of overall nonlinearity. If the processor 100 determines that the data is unreliable because the linear region is exceeded, the processor will initiate a calibration step. Finally, if the operator desires a calibration step, a button 104 is provided on the processor 100 for initiating calibration manually.

Step 736 predicts a new pulse pressure $P_p(pred)$ by multiplying the exciter waveform pressure $P_w$ by the ratio of the detected pulsatile voltage $V_p$ to the detected exciter waveform magnitude $V_w$.

$$P_p(pred) = P_w * \left( \frac{V_p}{V_w} \right)$$

This prediction uses the noninvasive sensor exciter waveform to determine the pressure difference between the diastole and systole of the natural blood pressure waveform. For example, if a noninvasive sensor exciter magnitude $V_w$ of 0.3 V relates to a pressure variation $P_w$ of 1 mm Hg and the noninvasive sensor waveform $V_p$ varies from –6 V to –6 V, then the noninvasive sensor waveform represents a pulse pressure excursion $P_p(pred)$ of 40 mm Hg.

Step 760 predicts a new systolic pressure $P_s(pred)$ by adding the predicted diastolic $P_D(Pred)$ and pulse pressures $P_p(pred)$.

$$P_s(pred) = P_D(pred) + P_p(pred)$$

In the above example if the diastole $P_D$(pred) is 80 mm Hg (DC offset) and the pulse $P_p$(pred) represents a difference of 40 mm Hg then the new systolic $P_s$(pred) is 120 mm Hg.

For display purposes the values determined for $P_s$(pred) and $P_D$(pred) can be displayed numerically. Similarly, the output waveform for display 102 can be displayed by scaling the noninvasive sensor natural blood pressure waveform prior to output using gain and offset scaling factors so that the output waveform has amplitude, $P_p$(pred), and DC offset, $P_D$(pred), equal to those predicted in the above process. The scaled output waveform signal can also be output to other instruments such as monitors, computers, processors and displays to be used for display, analysis or computational input.

Step 750 is taken when step 734 determines that the prior calibration is no longer reliable as described above. A calibration step activates the oscillometric cuff 201 and determines the patient's blood pressure, as described above. The processor 100 uses the calibration measurements to store updated pressure and waveform information relating to the DC offset, blood pressure waveform and exciter waveform. The updated variables include calibration pressure $P_p$(cal), calibration pulse exciter sensor waveform magnitude $V_e$(cal), diastolic pressure $P_{D0}$, diastolic exciter waveform phase $\Phi w_{D0}$, the rate of change of exciter waveform phase to pressure $D(\Phi w_D)/DP$ and calibration exciter waveform pressure $P_w$(cal).

$$P_w(cal) = P_p(cal) * \left( \frac{V_w}{V_p} \right)$$

A second embodiment is similar to the first and further induces a second exciter waveform into the arterial blood. An example second exciter waveform is one that has a frequency different from that of the first exciter waveform. It is noted that although the discussion of the second embodiment concentrates on a second exciter wave, any number of two or more exciter waves can be used to determine the perturbation velocity measurement.

In operation, processor 100 generates two exciter waveforms and communicates the waveforms to the exciter 202 via air tube 107. The exciter 202 responds by inducing both exciter waveforms into the patient. Noninvasive sensor 210 generates a signal responsive to a hemoparameter and transmits the signal to the processor 100 via wire 109.

The processor filters the noninvasive sensor signal into components of the natural waveform, a first exciter waveform, a second exciter waveform and noise. The processor determines the phase relationship of the first exciter waveform to a first reference input and determined the phase relationship of the second exciter waveform to a second reference input.

Once the processor has determined the phase of the exciter waveforms, the processor then generates a plurality of points, the slope of which relates to the velocity of the exciter waveform. This is shown in FIG. 8c, where the slope of the line is $-2\pi d/c$, and where d is distance and c is velocity. Since the distance is fixed and the slope is related to blood pressure, and since the slope changes based on changes in blood pressure, the velocity of the exciter waveform is determined.

Once the velocity is determined, a prediction of blood pressure is made according to FIG. 8a, showing the relationship of velocity to pressure. Thus, it is possible to determine the blood pressure with few, or zero, calibrations.

Figure 9:
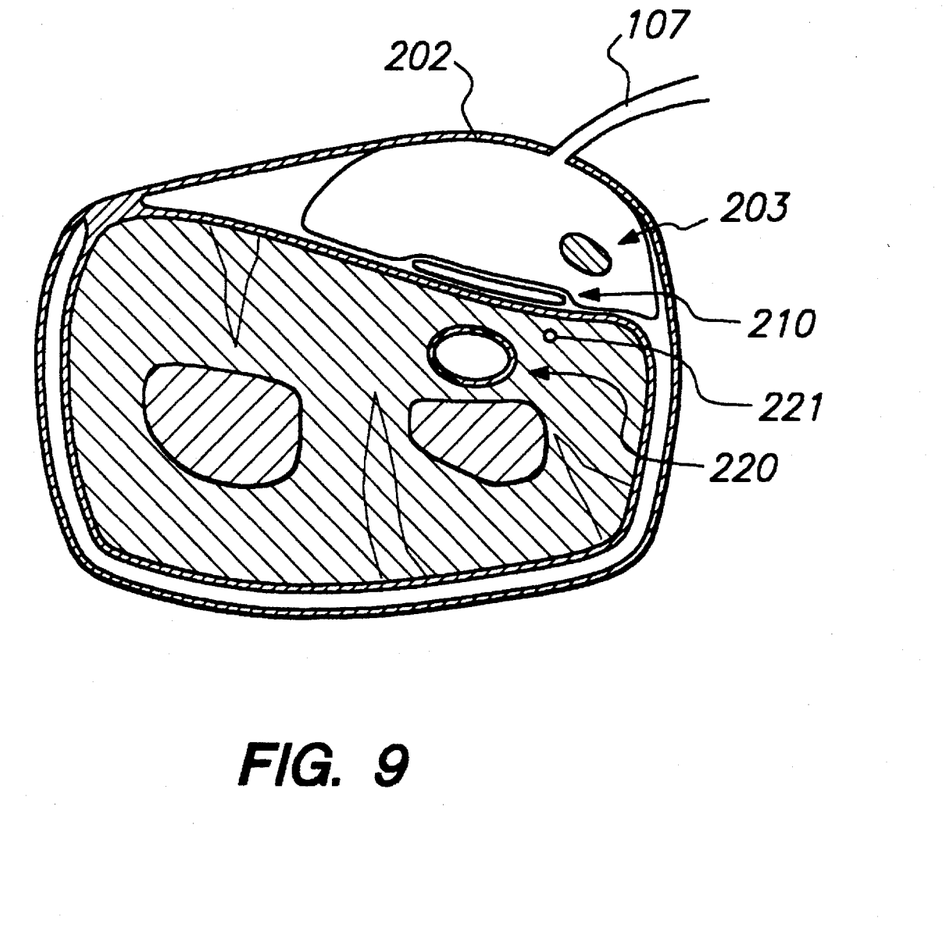
FIG. 9 depicts an exciter and noninvasive sensor attached to a patient.

A third embodiment is depicted in FIG. 9 showing a cross section of an exciter 202 and noninvasive sensor 210 at the same position above the blood vessel 220. The proximate location of the exciter and the sensor permits measurement of the blood vessel's response to the perturbations. In this embodiment, the noninvasive sensor is responsive to a hemoparameter such as blood flow or blood volume. These parameters can be measured with a sensor such as a photoplethysmograph. Detected changes in the blood vessel due to the natural pulsatile pressure are calibrated using external exciter pressure oscillations and compared against the sensor signal by the processor.

VARIATIONS ON THE DISCLOSED EMBODIMENTS

A close relationship between physiological parameters and hemoparameters supplies valuable information used in the present invention. The perturbation of body tissue and sensing the perturbation also supplied valuable information used in the present invention. Although the preferred embodiment concentrates on blood pressure, the present invention can also be used to analyze and track other physiological parameters such as vascular wall compliance, changes in the strength of ventricular contractions, changes in vascular resistance, changes in fluid volume, changes in cardiac output, myocardial contractility and other related parameters.

Calibration signals for the present invention can be obtained from a variety of sources including a catheter, manual determination, or other similar method.

The DC offset for the physiological parameter waveform can be obtained in a variety of ways for use with the present invention.

The exciter of the preferred embodiment uses air, but any suitable fluid can be used. Moreover, various exciter techniques can be used for inducing an exciter waveform into the patient such as an acoustic exciter, an electromagnetic exciter and an electromechanical exciter (e.g. piezoelectric device).

Various noninvasive sensors have been developed for sensing hemoparameters. These sensor types include piezoelectric, piezoresistive, impedance plethysmograph, photoplethysmograph, various types of strain gages, air cuffs, tonometry, conductivity, resistivity and other devices. The present invention can use any sensor that provides a waveform related to the hemoparameter of interest.

Having disclosed a preferred embodiment and the best mode, modifications and variations may be made to the disclosed embodiments without departing from the subject and spirit of the invention as defined by the following claims.

What is claimed is:

1. A monitor for determining a patient's physiological parameter, comprising:

a calibration device configured to provide a calibration signal representative of the patient's physiological parameter;

an exciter, positioned over a blood vessel of the patient, for inducing a transmitted exciter waveform into the patient;

a noninvasive sensor, positioned over said blood vessel, said noninvasive sensor configured to sense a hemoparameter and to generate a noninvasive sensor signal representative of said hemoparameter containing a component of a received exciter waveform;

a processor configured to determine a relationship between a property of said received exciter waveform and a property of the physiological parameter; and wherein said processor is connected to receive said calibration signal and said noninvasive sensor signal, said processor configured to determine said physiological parameter based at least in part on said calibration signal, said noninvasive sensor signal, and said relationship.

2. The monitor of claim 1, wherein:

said processor includes a filter configured to separate from said noninvasive sensor signal a component of one of the group consisting of said physiological parameter waveform, said received exciter waveform, signal exciter waveform and a noise waveform.

3. The monitor of claim 1, wherein:

said processor includes a filter configured to separate from said noninvasive sensor signal a component having a time-varying phase.

4. The monitor of claim 1, wherein:

said processor includes a filter configured to determine an arc representing time varying positions of said received exciter waveform, to determine a center point of said arc and to determine a noise vector from an origin to said center point; and said processor is configured to determine an arc vector from said center point to said time varying positions, where said arc vector has an arc vector angle that moves from a first angle to a second angle over time; and wherein said processor is configured to process said arc vector angle to determine the physiological parameter.

5. The monitor of claim 1, wherein:

said exciter is further configured to induce a second transmitted exciter waveform into the patient; and said processor includes a filter configured to separate from said noninvasive sensor signal a component of one of the group consisting of said physiological parameter waveform, said received exciter waveform, a second received exciter waveform, a signal exciter waveform, second signal exciter waveform and a noise waveform.

6. The monitor of one of claims 1, 2, 3 or 4, wherein:

said processor is further configured to determine a relationship between a component of said received exciter waveform and an amplitude and DC offset of the physiological parameter.

7. The monitor of one of claims 1, 2, 3 or 4, wherein:

said processor is further configured to determine a relationship between an amplitude and phase of a component of said received exciter waveform and an amplitude and DC offset of the physiological parameter.

8. The monitor of one of claims 1, 2, 3, 4 or 5, wherein:

said processor is responsive to said noninvasive sensor signal, and further configured to determine the validity of said calibration signal and to initiate a calibration when said calibration signal is not valid.

9. The monitor of one of claims 1, 2, 3, 4 or 5, wherein:

said processor is further configured to scale said physiological parameter waveform based on the relationship between a property of said received exciter waveform and a property of the physiological parameter and to generate a scaled physiological parameter waveform signal.

10. A processor for determining a patient's physiological parameter with an apparatus having a calibration device configured to provide a calibration signal representative of the patient's physiological parameter, an exciter positioned over a blood vessel of the patient for inducing a transmitted exciter waveform into the patient, and a noninvasive sensor positioned over said blood vessel, said noninvasive sensor configured to sense a hemoparameter and to generate a noninvasive sensor signal representative of said hemoparameter, said processor comprising:

a first input configured to receive said calibration signal;

a second input configured to receive said noninvasive sensor signal;

a filter configured to separate from said noninvasive sensor signal a component representing a received exciter waveform;

a relationship routine configured to determine a relationship between a property of said received exciter waveform and a property of said physiological parameter; and a determination routine configured to determine said physiological parameter based at least in part on said calibration signal, said noninvasive sensor signal, and said relationship.

11. The processor of claim 10, wherein:

said filter is configured to separate from said noninvasive sensor signal a component having a time-varying phase.

12. The processor of claim 10, wherein:

said filter is configured to determine an arc representing time varying positions of said received exciter waveform, to determine a center point of said arc and to determine a noise vector from an origin to said center point; and said filter is configured to determine an arc vector from said center point to said time varying positions, where said arc vector has an arc vector angle that moves from a first angle to a second angle over time; and wherein said determination routine is configured to process said arc vector angle to determine the physiological parameter.

13. The processor of one of claims 10, 11 or 12, wherein:

said determination routine is further configured to compare a phase relationship between said transmitted exciter waveform and a component of said noninvasive sensor signal to determine the physiological parameter.

14. The processor of one of claims 10, 11 or 12, wherein:

said filter is further configured to separate from said noninvasive sensor signal a component representing a second received exciter waveform.

15. The processor of one of claims 10, 11 or 12, wherein:

said determination routine is further configured to compare a phase relationship between said transmitted exciter waveform and a component of said noninvasive sensor signal, and to compare a phase relationship between a second transmitted exciter waveform and a component of said noninvasive sensor signal to determine the physiological parameter.

16. A method of determining a patient's physiological parameter, comprising the steps of:

providing a calibration signal representative of the patient's physiological parameter and storing the calibration signal;

inducing a transmitted exciter waveform into the patient;

noninvasively sensing a hemoparameter, and generating a noninvasive sensor signal representative of said hemoparameter and containing a component of a received exciter waveform;

determining a relationship between a property of said received exciter waveform and a property of the physiological parameter; and determining said physiological parameter based at least in part on said calibration signal, said non-invasive sensor signal, and said relationship.

17. The method of claim 16, wherein:

said processing step includes a filtering step of separating from said noninvasive sensor signal a component of one of the group consisting of said physiological parameter waveform, said received exciter waveform, signal exciter waveform and a noise waveform.

18. The method of claim 16, wherein:

said processing step includes a filtering step of separating from said noninvasive sensor signal a component having a time-varying phase.

19. The method of claim 16, wherein:

said processing step includes a filtering step of determining an arc representing time varying positions of said received exciter waveform, determining a center point of said arc and determining a noise vector from an origin to said center point; and said processing step includes a filtering step of determining an arc vector from said center point to said time varying positions, where said arc vector has an arc vector angle that moves from a first angle to a second angle over time.

20. The method of claim 16, further comprising:

inducing a second transmitted exciter waveform into the patient; and wherein said processing step includes a filtering step of separating from said noninvasive sensor signal a component of one of the group consisting of said physiological parameter waveform, said received exciter waveform, a second received exciter waveform, a signal exciter waveform, second signal exciter waveform and a noise waveform.

21. The method of one of claims 16, 17, 18 or 19, wherein:

said processing step includes determining a relationship between a component of said received exciter waveform and an amplitude and DC offset of the physiological parameter.

22. The method of one of claims 16, 17, 18 or 19, wherein:

said processing step includes determining a relationship between an amplitude and phase of a component of said received exciter waveform and an amplitude and DC offset of the physiological parameter.

23. The method of one of claims 16, 17, 18, 19 or 20, wherein:

said processing step includes determining the validity of said calibration signal and initiating said step of providing a calibration signal when said calibration signal is not valid.

24. The method of one of claims 16, 17, 18, 19 or 20, wherein:

said processing step includes scaling said physiological parameter waveform based on the relationship between a property of said received exciter waveform and a property of the physiological parameter and generating a scaled physiological parameter waveform signal.

25. A monitor for determining a patient's blood pressure, comprising:

an inflatable cuff positioned on an extremity of the patient and configured to provide a calibration signal representative of the patient's physiological parameter;

an exciter positioned over a blood vessel of the patient and configured to induce a transmitted exciter waveform into the patient;

a noninvasive sensor, positioned over said blood vessel and at a distance from said exciter, said noninvasive sensor configured to sense a hemoparameter and to generate a noninvasive sensor signal representative of said hemoparameter containing a component of a received exciter waveform;

a processor configured to determine a relationship between a property of said received exciter waveform and a property of said physiological parameter;

wherein said processor is connected to receive said calibration signal and said noninvasive sensor signal;

wherein said processor includes a filter configured to separate from said noninvasive sensor signal a component representing said received exciter waveform; and wherein said processor is configured to determine said physiological parameter based at least in part on said calibration signal, said noninvasive sensor signal, and said relationship.

26. The monitor of claim 25, further comprising:

an exciter sensor, positioned near said exciter and configured to sense said transmitted exciter waveform and generating an exciter sensor signal representative of said transmitted exciter waveform, and wherein said processor is further configured to compare the phase relationship of said transmitted exciter sensor signal and said received exciter waveform to determine said blood pressure.

* * * * *